United States Patent
Foster et al.

(10) Patent No.: US 9,044,140 B2
(45) Date of Patent: Jun. 2, 2015

(54) PHOTODYNAMIC THERAPY WITH SPATIALLY RESOLVED DUAL SPECTROSCOPIC MONITORING

(75) Inventors: Thomas H. Foster, Rochester, NY (US); William J. Cottrell, Dallas, TX (US); Chad Bigelow, Somerville, MA (US); Allan R. Oseroff, Buffalo, NY (US)

(73) Assignee: University of Rochester, Rochester, NY (US)

( * ) Notice: Subject to any disclaimer, the term of this patent is extended or adjusted under 35 U.S.C. 154(b) by 1838 days.

(21) Appl. No.: 11/631,121

(22) PCT Filed: Jun. 30, 2005

(86) PCT No.: PCT/US2005/023573
§ 371 (c)(1),
(2), (4) Date: Aug. 27, 2008

(87) PCT Pub. No.: WO2006/025940
PCT Pub. Date: Mar. 9, 2006

(65) Prior Publication Data
US 2009/0043296 A1   Feb. 12, 2009

Related U.S. Application Data

(60) Provisional application No. 60/583,786, filed on Jun. 30, 2004.

(51) Int. Cl.
*A61B 18/18* (2006.01)
*A61B 5/00* (2006.01)
*A61N 5/06* (2006.01)

(52) U.S. Cl.
CPC ............ *A61B 5/0059* (2013.01); *A61N 5/0601* (2013.01); *A61N 5/062* (2013.01)

(58) Field of Classification Search
CPC .......... A61B 2018/00642; A61B 2018/00648; A61B 2018/00773; A61B 2018/00785
USPC ..................... 606/1–19; 607/88–95
See application file for complete search history.

(56) References Cited

U.S. PATENT DOCUMENTS

| 4,768,513 A | * | 9/1988 | Suzuki ......................... 600/476 |
| 4,913,142 A | | 4/1990 | Kittrell et al. |

(Continued)

FOREIGN PATENT DOCUMENTS

| DE | 2521659 A1 | 12/1976 |
| DE | 4240769 | 6/1994 |

(Continued)

OTHER PUBLICATIONS

Benirschke K, K.P. "Architecture of Normal Villous Trees," Chapter 7, Pathology of the Human Placenta, 2002, Springer Verlag, New York, NY, pp. 116-154.
(Continued)

*Primary Examiner* — William Thomson
*Assistant Examiner* — John R Downey
(74) *Attorney, Agent, or Firm* — Patent Technologies, LLC; Robert D. Gunderman, Jr.

(57) ABSTRACT

An instrument for photodynamic therapy applies treatment light from a dye laser, white light, and ultraviolet fluorescence excitation light from an LED onto a lesion and surrounding areas in a time-multiplexed manner. The reflected white light is analyzed in a spectrometer to determine a correction for the dynamic optical spectral properties of the patient's tissue. Light emitted by fluorescence from the lesion and the surrounding areas is analyzed in another spectrometer, and the results are corrected in a computer, using the correction. An optical switch has been developed for the instrument, using a bistable solenoid and a sled.

18 Claims, 5 Drawing Sheets

(56) References Cited

U.S. PATENT DOCUMENTS

| | | | |
|---|---|---|---|
| 5,035,482 A * | 7/1991 | ten Berge et al. | 385/16 |
| 5,098,804 A * | 3/1992 | Booth | 430/1 |
| 5,278,692 A | 1/1994 | Delapierre | |
| 5,413,197 A | 5/1995 | Baer et al. | |
| 5,433,204 A | 7/1995 | Olson | |
| 5,483,958 A | 1/1996 | Merberg et al. | |
| 5,533,508 A | 7/1996 | Doiron | |
| 5,534,997 A | 7/1996 | Schrader | |
| 5,537,499 A | 7/1996 | Brekke | |
| 5,907,395 A | 5/1999 | Schulz et al. | |
| 6,070,093 A * | 5/2000 | Oosta et al. | 600/316 |
| 6,102,857 A | 8/2000 | Kruger | |
| 6,130,071 A | 10/2000 | Alitalo et al. | |
| 6,219,566 B1 * | 4/2001 | Weersink et al. | 600/317 |
| 6,238,348 B1 | 5/2001 | Crowley et al. | |
| 6,377,841 B1 * | 4/2002 | Lin et al. | 600/477 |
| 6,384,951 B1 | 5/2002 | Basiji et al. | |
| 6,477,289 B1 * | 11/2002 | Li | 385/16 |
| 6,571,118 B1 * | 5/2003 | Utzinger et al. | 600/476 |
| 6,572,609 B1 * | 6/2003 | Farr et al. | 606/15 |
| 6,593,101 B2 | 7/2003 | Richards-Kortum et al. | |
| 6,615,063 B1 * | 9/2003 | Ntziachristos et al. | 600/312 |
| 7,037,325 B2 | 5/2006 | Svanberg et al. | |
| 7,399,278 B1 | 7/2008 | Ross | |
| 7,443,491 B2 * | 10/2008 | Kanda | 356/73 |
| 7,606,394 B2 | 10/2009 | Mirtsching | |
| 7,613,330 B2 | 11/2009 | Mirtsching et al. | |
| 7,697,145 B2 * | 4/2010 | Izatt | 356/497 |
| 2001/0047136 A1 | 11/2001 | Domanik et al. | |
| 2002/0035361 A1 | 3/2002 | Houser et al. | |
| 2002/0045811 A1 | 4/2002 | Kittrell et al. | |
| 2002/0118870 A1 | 8/2002 | Youvan et al. | |
| 2002/0123023 A1 | 9/2002 | Sicurelli et al. | |
| 2002/0138073 A1 | 9/2002 | Intintoli et al. | |
| 2002/0141625 A1 | 10/2002 | Nelson | |
| 2003/0009205 A1 | 1/2003 | Biel | |
| 2003/0013973 A1 | 1/2003 | Georgakoudi et al. | |
| 2003/0018324 A1 | 1/2003 | Davenport et al. | |
| 2003/0099166 A1 | 5/2003 | Chan et al. | |
| 2003/0199860 A1 | 10/2003 | Loeb et al. | |
| 2003/0228566 A1 * | 12/2003 | Mao et al. | 435/4 |
| 2003/0232445 A1 * | 12/2003 | Fulghum, Jr. | 436/63 |
| 2004/0044287 A1 | 3/2004 | Lin et al. | |
| 2004/0095855 A1 | 5/2004 | Minase | |
| 2004/0155049 A1 | 8/2004 | Float et al. | |
| 2004/0172163 A1 | 9/2004 | Varis | |
| 2004/0243123 A1 | 12/2004 | Grasso et al. | |
| 2005/0182392 A1 | 8/2005 | Brucker et al. | |
| 2005/0203353 A1 | 9/2005 | Ma et al. | |
| 2007/0299341 A1 | 12/2007 | Wang et al. | |
| 2008/0123083 A1 | 5/2008 | Wang et al. | |
| 2008/0192897 A1 | 8/2008 | Piorek et al. | |
| 2009/0023168 A1 | 1/2009 | Park et al. | |
| 2009/0024043 A1 | 1/2009 | MacLeod et al. | |
| 2009/0252392 A1 | 10/2009 | Panarace | |

FOREIGN PATENT DOCUMENTS

| | | |
|---|---|---|
| EP | 0323920 | 7/1989 |
| EP | 0521797 | 1/1993 |
| GB | 2157842 | 10/2008 |
| WO | WO-9321842 A1 | 11/1993 |
| WO | WO-96/20683 | 7/1996 |
| WO | WO-99/17668 | 4/1999 |
| WO | WO-2004100761 A2 | 11/2004 |

OTHER PUBLICATIONS

Kaufmann, et al., "Aspects of human fetoplacental vasculogenesis and angiogenesis: II. Changes during normal pregnancy," Placenta, 2004, pp. 114-126, vol. 25, Elsevier, Maryland Heights, MO, USA. Ltd., Maryland Heights, MO, USA.

Demir, et al., "Classification of human placental stem villi: review of structural and functional aspects," Microscopy Research and Technique, 1997, pp. 29-41, vol. 38, Wiley, Hoboken, NJ, USA.

Kosanke, et al., "Branching patterns of human placental villous trees: perspectives of topological analysis," Placenta, 1993, pp. 591-604, vol. 14, Elsevier, Maryland Heights, MO, USA.

Kaufmann, et al., "Classification of human placental villi: I. Histology," Cell and Tissue Research, 1979, pp. 409-423, vol. 200, Springer, New York, NY, USA.

Kingdom, et al., "Development of the placental villous tree and its consequences for fetal growth," European Journal of Obstetrics & Gynecology and Reproductive Biology, 2000, pp. 35-43, vol. 92, Elsevier, Maryland Heights, MO, USA.

Charnock-Jones, et al., "Aspects of human fetoplacental vasculogenesis and angiogenesis: I. Molecular regulation," Placenta, 2004, pp. 103-113, vol. 25, Elsevier, Maryland Heights, MO, USA.

Mayhew, et al., "Aspects of human fetoplacental vasculogenesis and angiogenesis: III. Changes in complicated pregnancies," Placenta, 2004, pp. 127-139, vol. 25, Elsevier, Maryland Heights, MO, USA.

Demir, et al., "Fetal vasculogenesis and angiogenesis in human placental villi," Acta Anat, 1989, pp. 190-203, vol. 136, Karger AG, Basel, Switzerland.

Benirschke, "Basic Structure of the Villous Trees," Chapter 6 in the Pathology of the Placenta, 2002, pp. 50-115, Springer-Verlag, New York, USA.

Benirschke, "Angioarchitecture of Villi," in The Pathology of the Placenta, 2002, pp. 134-140, Springer-Verlag, New York, USA.

Grether, et al., "Reliability of placental histology using archived specimens," Paediatric Perinatal Epidemiology, 1999, pp. 489-495, vol. 13, Wiley, Hoboken, NJ, USA.

Khong, et al., "Observer reliability in assessing placental maturity by histology," Journal of Clinical Pathology, 1995, pp. 420-423, vol. 48, BMJ, London, UK.

Khong, "Placental vascular development and neonatal outcome," Seminars in Neonatology, 2004, pp. 255-263, vol. 9, Elsevier, Maryland Heights, MO, USA.

Jaddoe, et al., "Hypotheses on the fetal origins of adult diseases: contributions of epidemiological studies," European Journal of Epidemiology, 2006, pp. 91-102, vol. 21, Springer, New York, NY, USA.

De Boo, et al., "The developmental origins of adult disease (Barker) hypothesis," Australian and New Zealand Journal of Obstetrics and Gynaecology, 2006, pp. 4-14, vol. 46, Wiley, Hoboken, NJ, USA.

Barker, et al., "The developmental origins of insulin resistance," Hormone Research, 2005, pp. 2-7, vol. 64, suppl 3, Karger AG, Basel, Switzerland.

Levitt, et al., "The foetal origins of the metabolic syndrome—a South African perspective," Cardiovascular Journal of South Africa, 2002, pp. 179-180, vol. 13, No. 4, Durbanville, South Africa.

Barker, "The fetal origins of type 2 diabetes mellitus," Annals of Internal Medicine, 1999, pp. 322-324, vol. 130, No. 4, pt. 1, Philadelphia, PA, USA.

Adair, et al., "Developmental determinants of blood pressure in adults," Annual Review of Nutrition, 2005, pp. 407-434, vol. 25, Palo Alto, CA, USA.

Levitt, et al., "Adult BMI and fat distribution but not height amplify the effect of low birthweight on insulin resistance and increased blood pressure in 20-year-old South Africans," Diabetologia, 2005, pp. 1118-1125, vol. 48, Springer, New York, NY, USA.

Levitt, et al., "An inverse relation between blood pressure and birth weight among 5 year old children from Soweto, South Africa," Journal of Epidemiology and Community Health, 1999, pp. 264-268. vol. 53, BMJ, London, UK.

Barker, et al., "The intrauterine and early postnatal origins of cardiovascular disease and chronic bronchitis," Journal of Epidemiology and Community Health, 1989, pp. 237-240, vol. 43, BMJ, London, UK.

Barker, et al., "The maternal and fetal origins of cardiovascular disease," Journal of Epidemiology and Community Health, 1992, pp. 8-11, vol. 46, BMJ, London, UK.

Tanis, et al., "Dutch women with a low birth weight have an increased risk of myocardial infarction later in life: a case control study," Reproductive Health, 2005, p. 1, vol. 2, No. 1.

Rich-Edwards, et al., "Longitudinal study of birth weight and adult body mass index in predicting risk of coronary heart disease and stroke in women," BMJ Online First, 2005, 300 p. 1115, BMJ, London, UK.

(56) References Cited

OTHER PUBLICATIONS

Lawlor, et al., "Birth weight is inversely associated with incident coronary heart disease and stroke among individuals born in the 1950s: findings from the Aberdeen Children of the 1950s prospective cohort study," Circulation, 2005, pp. 1414-1418, vol. 112, Lippincott Williams & Wilkins, Hagerstown, MD, USA.
Cooper, et al., "Review: developmental origins of osteoporotic fracture," Osteoporosis International, 2005, pp. 337-347, vol. 17, Springer, New York, NY, USA.
Gluckman, et al., "Life-long echoes—a critical analysis of the developmental origins of adult disease model," Biology of the Neonate, 2005, pp. 127-139, vol. 87, Karger AG, Basel, Switzerland.
Jasienska, et al., "High ponderal index at birth predicts high estradiol levels in adult women," American Journal of Human Biology, 2006, pp. 133-140, vol. 18, Wiley, Hoboken, NJ, USA.
Lagiou, et al., "Diet during pregnancy and levels of maternal pregnancy hormones in relation to the risk of breast cancer in the offspring," European Journal of Cancer Prevention, 2006, pp. 20-26, vol. 15, Lippincott Williams & Wilkins, Hagerstown, MD, USA.
Lagiou, et al., "Maternal height, pregnancy estriol and birth weight in reference to breast cancer risk in Boston and Shanghai," International Journal of Cancer, 2005, pp. 494-498, vol. 117, Wiley, Hoboken, NJ, USA.
Nilsen, et al., "Birth size and subsequent risk for prostate cancer: a prospective population-based study in Norway," International Journal of Cancer, 2005, pp. 1002-1004, vol. 113, Wiley, Hoboken, NJ, USA.
Asbury, et al., "Birthweight-discordance and differences in early parenting relate to monozygotic twin differences in behaviour problems and academic achievement at age 7," Developmental Science, 2006, pp. F22-F31, vol. 9, No. 2, Wiley, Hoboken, NJ, USA.
Bellingham-Young, et al., "Prematurity and adult minor illness," Neuroendocrinology Letters, 2004, pp. 117-126, vol. 25, suppl. 1, Society of Integrated Sciences.
Nilsson, et al., "Fetal growth restriction and schizophrenia: a Swedish twin study," Twin Research and Human Genetics, 2005, pp. 402-408, vol. 8, No. 4. Australian Academic Press, Bowen Hills, Australia.
Gunnell, et al., "The association of fetal and childhood growth with risk of schizophrenia. Cohort study of 720,000 Swedish men and women," Schizophrenia Research, 2005, pp. 315-322, vol. 79, Elsevier, Maryland Heights, MO, USA.
Willinger, et al., "Neurodevelopmental schizophrenia: obstetric complications, birth weight, premorbid social withdrawal and learning disabilities," Neuropsychobiology, 2001, pp. 163-169, vol. 43, Karger AG, Basel, Switzerland.
Talbert, "Uterine flow velocity waveform shape as an indicator of maternal and placental development failure mechanisms: a model-based synthesizing approach," Ultrasound in Obstetrics and Gynecology, 1995, pp. 261-271, vol. 6, Wiley, Hoboken, NJ, USA.
Naeye, "Disorders of the Placenta and Decidua," in Disorders of the Placenta, Fetus and Neonata, 1992, pp. 129-134, Mosby Year Book: Philadelphia, PA, USA.
Benirschke, "Placental Shape Aberrations," Chapter 13, in Pathology of the Human Placenta, 2002, pp. 401-404, Springer, New York, NY, USA.
Naeye, "Disorders of the Placenta and Decidua," in Disorders of the Placenta, Fetus and Neonata, 1992, pp. 129-130, Mosby Year Book: Philadelphia, PA, USA.
Benirschke, "Classification of Villous Maldevelopment," Chapter 15, in Pathology of the Human Placenta, 2002, pp. 437-460, Springer, New York, NY, USA.
Kaufmann, et al., "Cross-sectional features and three-dimensional structure of human placental villi," Placenta, 1987, pp. 235-247, vol. 8, Elsevier, Maryland Heights, MO, USA. Ltd., Maryland Heights, MO, USA.
Schweikhart, et al., "Morphology of placental villi after premature delivery and its clinical relevance," Archives of Gynecology, 1986, pp. 101-114, vol. 239, Springer, New York, NY, USA.
Larsen, et al., "Stereologic examination of placentas from mothers who smoke during pregnancy," American Journal of Obstetrics & Gynecology, 2002, pp. 531-537, vol. 186, Elsevier, Maryland Heights, MO, USA.
Mayhew, "Changes in fetal capillaries during preplacental hypoxia: growth, shape remodelling and villous capillarization in placentae from high-altitude pregnancies," Placenta, 2003, pp. 191-198, vol. 24, Elsevier, Maryland Heights, MO, USA.
Reshetnikova, et al., "Placental histomorphometry and morphometric diffusing capacity of the villous membrane in pregnancies complicated by maternal iron-deficiency anemia," American Journal of Obstetrics & Gynecology, 1995, pp. 724-727, vol. 173, Elsevier, Maryland Heights, MO, USA.
Vickers, et al., "Fetal origins of hyperphagia, obesity, and hypertension and postnatal amplification by hypercaloric nutrition," American Journal of Physiology—Endocrinology and Metabolism, 2000, pp. E83-E87, vol. 279, The American Physiological Society, Bethesda, MD, USA.
Stocker, et al., "Fetal origins of insulin resistance and obesity," Proceedings of the Nutrition Society, 2005, pp. 143-151, vol. 64, Cambridge University Press, New York, NY, USA.
McMillen, et al., "Early origins of obesity: programming the appetite regulatory system," Journal of Physiology, 2005, pp. 9-17, vol. 565, The Physiological Society, Cambridge, UK.
Armitage, et al. "Experimental models of developmental programming: consequences of exposure to an energy rich diet during development," Journal of Physiology, 2005, pp. 3-8, vol. 565, The Physiological Society, Cambridge, UK.
Longo, "Fetal origins of adult vascular dysfunction in mice lacking endothelial nitric oxide synthase," American Journal of Physiology—Regulatory, Integrative and Comparative Physiology, 2005, pp. R1114-R1121, vol. 288, The American Physiological Society, Bethesda, MD, USA.
Horton, "Fetal origins of developmental plasticity: animal models of induced life history variation," Am J Hum Biol, pp. 34-43, 2005, vol. 17.
Bertram, et al., "Prenatal programming of postnatal endocrine responses by glucocorticoids," Reproduction, 2002, pp. 459-467, vol. 124, BioScientifica Ltd, Bradley Stoke, UK.
Green, "Programming of endocrine mechanisms of cardiovascular control and growth," Journal of the Society for Gynecologic Investigation, 2001, pp. 57-68, vol. 8, No. 2, SAGE Publications, Newbury Park, CA, USA.
McMillen, et al. "Developmental origins of the metabolic syndrome: prediction, plasticity, and programming," Physiological Review, 2005, pp. 571-633. vol. 85, The American Physiological Society, Bethesda, MD, USA.
Wu, et al., "Maternal nutrition and fetal development," The Journal of Nutrition, 2004, pp. 2169-2172, vol. 134, American Society for Nutrition, Bethesda, MD, USA.
Pham, et al., "Uteroplacental insufficiency increases apoptosis and alters p53 gene methylation in the full-term IUGR rat kidney," American Journal of Physiology—Regulatory, Integrative and Comparative Physiology, 2003, pp. R962-R970, vol. 285, The American Physiological Society, Bethesda, MD, USA.
Seckl, "Glucocorticoids, feto-placental 11 beta-hydroxysteroid dehydrogenase type 2, and the early life origins of adult disease,". Steroids, 1997, pp. 89-94, vol. 62, Elsevier, Maryland Heights, MO, USA.
Sibley, et al., "Placental phenotypes of intrauterine growth," Pediatric Research, 2005, vol. 58, pp. 827-832, International Pediatric Research Foundation, Inc., Lippincott Williams & Wilkins, Hagerstown MD, USA.
Randhawa, et al., "The role of the insulin-like growth factor system in prenatal growth," Molecular Genetics and Metabolism, 2005, pp. 84-90, vol. 86, Elsevier, Maryland Heights, MO, USA.
Wallace, et al., "Nutritionally mediated placental growth restriction in the growing adolescent: consequences for the fetus," Biology of Reproduction, 2004, pp. 1055-1062, vol. 71, The Society for the Study of Reproduction, Inc., Madison, WI, USA.
Baschat, et al., "Fetal growth restriction due to placental disease," Seminars in Perinatology, 2004, pp. 67-80, vol. 28, No. 1, Elsevier, Maryland Heights, MO, USA.

(56) References Cited

OTHER PUBLICATIONS

Resnik, "Intrauterine growth restriction," Obstetrics & Gynecology, 2002, pp. 490-496, vol. 99, Elsevier, Maryland Heights, MO, USA.
Morley, "Fetal origins of adult disease," Seminars in Fetal & Neonatal Medicine, 2006, pp. 73-78, vol. 11, Elsevier, Maryland Heights, MO, USA.
Lockwood, "The diagnosis of preterm labor and the prediction of preterm delivery," Clinical Obstetrics and Gynecology, 1995, pp. 675-687, vol. 38, No. 4, Lippincott Williams & Wilkins, Hagerstown, MD, USA.
Metzger, et al., "Genetic control of branching morphogenesis," Science Magazine, 1999, pp. 1635-1639, vol. 284, Washington, DC, USA.
Yevtodiyenko, et al., "Dlk1 expression marks developing endothelium and sites of branching morphogenesis in the mouse embryo and placenta," Developmental Dynamics, 2006, pp. 1115-1123, vol. 235, Wiley, Hoboken, NJ, USA.
Le Noble, et al., "Control of arterial branching morphogenesis in embryogenesis: go with the flow," Cardiovascular Research, 2005, vol. 65, pp. 619-628, Elsevier, Maryland Heights, MO, USA.
Warburton, et al., "Molecular mechanisms of early lung specification and branching morphogenesis," Pediatric Research, 2005, pp. 26R-37R, vol. 57, No. 5, pt. 2, Lippincott Williams & Wilkins, Hagerstown MD, USA.
Hu, et al., "Genetic regulation of branching morphogenesis: lessons learned from loss-of-function phenotypes," Pediatric Research, 2003, pp. 433-438, vol. 54, Lippincott Williams & Wilkins, Hagerstown MD, USA.
Ingelfinger, et al., "Perinatal programming, renal development, and adult renal function," American Journal of Hypertension, 2002, pp. 46S-49S vol. 15, No. 2, pt. 2, Elsevier, Maryland Heights, MO, USA.
Miettinen, "Epidermal growth factor receptor in mice and men—any applications to clinical practice?" Annals of Medicine, 1997, pp. 531-534, vol. 29, Informa PLC, St. Helier, Jersey.
Miettinen, et al., "Epithelial immaturity and multiorgan failure in mice lacking epidermal growth factor receptor," Nature, 1995, pp. 337-341, vol. 376, Nature Publishing Group, London, UK.
Grenander, "General Pattern Theory—a Mathematical Study of Regular Structures," 1993, pp. 539-544 and 740-784, Oxford University Press, Oxford, UK.
Amit, et al., "Structural image restoration through deformable templates,". Journal of the American Statistical Association, 1991, pp. 376-387, vol. 86, No. 414, American Statistical Association, Alexandria, VA, USA.
Grizzi, et al., "Estimate of Neovascular Tree Complexity by Microscopy Analysis," Current Issues on Multidisciplinary Microscopy Research and Education, 2005, pp. 140-149, Formatex, Badajoz, Spain.
Giles, "Benoit Mandelbrot: father of fractals," Nature, 2004, pp. 266-267, vol. 432, Nature Publishing Group, London, UK.
Meisel, "Generalized Mandelbrot rule for fractal sections," Physical Review A, 1992, pp. 654-656, vol. 45, No. 2, American Physical Society, College Park, MD, USA.
Keipes, et al., "Of the British coastline and the interest of fractals in medicine," Biomedicine & Pharmacotherapy, 1993, pp. 409-415, vol. 47, Elsevier, Maryland Heights, MO, USA.
Porter, et al., "A fractal analysis of pyramidal neurons in mammalian motor cortex," Neuroscience Letters, 1991, pp. 112-116, vol. 130, Elsevier, Maryland Heights, MO, USA.
Mayhew, et al., "Stereological investigation of placental morphology in pregnancies complicated by pre-eclampsia with and without intrauterine growth restriction," Placenta, 2003, pp. 219-226, vol. 24, Elsevier, Maryland Heights, MO, USA.
Byrne, "Factor analytic models: viewing the structure of an assessment instrument from three perspectives," Journal of Personality Assessment, 2005, pp. 17-32, vol. 85, Informa PLC, St. Helier, Jersey.
Coste, et al., "Methodological issues in determining the dimensionality of composite health measures using principal component analysis: case illustration and suggestions for practice," Quality of Life Research, 2005, pp. 641-654, vol. 14, Springer, New York, NY, USA.
Bentler, et al., "Structural equation models in medical research," Statistical Methods in Medical Research, 1992, pp. 159-181, vol. 1, SAGE Publications, Newbury Park, CA, USA.
Pembrey, "The Avon Longitudinal Study of Parents and Children (ALSPAC): a resource for genetic epidemiology," European Journal of Endocrinology, 2004, pp. U125-U129, vol. 151, BioScientifica Ltd, Bristol, UK.
Patel, et al., "Prenatal risk factors for Caesarean section. Analyses of the ALSPAC cohort of 12,944 women in England," International Journal of Epidemiology, 2005, pp. 353-367, vol. 34, Oxford University Press, Oxford, UK.
Headley, et al., "Medication use during pregnancy: data from the Avon Longitudinal Study of Parents and Children," European Journal of Clinical Pharmacology, 2004, pp. 355-361, vol. 60, Springer, New York, NY, USA.
Fergusson, et al., "Maternal use of cannabis and pregnancy outcome," BJOG: An International Journal of Obstetrics and Gynaecology, 2002, pp. 21-27, vol. 109, Wiley, Hoboken, NJ, USA.
Golding, "Outcome of pregnancy in diabetic women—more investigation is needed into whether control of diabetes is really poorer in England than Norway," BMJ, 2001, pp. 614-615, vol. 322, BMJ Group, London, UK.
Dorosty, et al., "Factors associated with early adiposity rebound," Pediatrics, 2000, pp. 1115-1118, vol. 105, American Academy of Pediatrics, Elk Grove Village, IL, USA.
Rogers, et al., "Financial difficulties, smoking habits, composition of the diet and birthweight in a population of pregnant women in the South West of England," European Journal of Clinical Nutrition, 1998, pp. 251-260, vol. 52, Nature Publishing Group, London, UK.
Farrow, et al., "Birthweight of term infants and maternal occupation in a prospective cohort of pregnant women," Occupational and Environmental Medicine, 1998, pp. 18-23, vol. 55, BMJ Group, London, UK.
Maitra, et al., "Mode of delivery is not associated with asthma or atopy in childhood," Clinical and Experimental Allergy, 2004, pp. 1349-1355, vol. 34, Wiley, Hoboken, NJ, USA.
Golding, "Children of the nineties—a longitudinal study of pregnancy and childhood based on the population of Avon (ALSPAC)," West of England Medical Journal, 1990, pp. 80-82, vol. 105.
Carey, "Infant Temperament Questionnaire (4-8 months)," Philadelphia: Dept. Educational Psychology, Temple University, 1977.
Fullard, et al., "Toddler Tempermant Scale (1-3 year old children . . . ," Philadelphia, PA: Dept. Educational Psychology, Temple University, 1978.
Buss, et al., "The EAS Temperament Scale," in Temperament: Early Developing Personality Traits, 1984, Hillsdale, NJ, USA.
Goodman, "The Strengths and Difficulties Questionnaire: a Research Note . . . ," Journal of Child Psychology and Psychiatry, 1997, pp. 581-586, vol. 38, No. 5, Wiley, Hoboken, NJ, USA.
Frankenburg, et al., "The Denver Developmental Screening Test," Journal of Pediatrics, 1967, pp. 181-191, vol. 71, No. 2, Elsevier, Maryland Heights, MO, USA.
Griffiths, "Administering the Scale," in The Abilities of Babies—A Study in Mental Measurement, 1954, pp. 117-182, McGraw-Hill, New York, NY, USA.
Fenson, et al., "Technical Manual for the MacArthur Communicative Development Inventories," 1991, San Diego, CA: Development Psychology Laboratory.
Miller, et al., "A Mathematical textbook of deformable neuro-anatomies . . . ," Proceedings of the National Academy of Sciences, 1993, pp. 11944-11948, National Academy of Sciences, Washington, DC, USA.
Hastie, et al., "Elements of Statistical Learning: Data Mining, Inference, and Prediction," 2001, pp. 1-40, Springer, New York, NY, USA.
Penev, et al., "Local feature analysis: a general statistical theory for object representation . . . ," Network: Computation in Neural Systems, 1996, pp. 477-500, vol. 7, Informa PLC, St. Helier, Jersey.
Small, C., The Statistical Theory of Shape. 1996, New York: Springer.
Dryden, I.L.M., KV. , Statistical Shape Analysis. 1998, New York: Wiley Press.

(56) References Cited

OTHER PUBLICATIONS

Lele, S.R., JT., An Invariant Approach to Statistical Analysis of Shapes. 2000, London, UK.: Chapman and Hall/CRC Press.
McKeague, I., A Statistical Model for Signature Verification. . Journal of the American Statistical Association, 2005. 100: p. 231-241.
Benirschke K, K.P., Normative Values and Tables (Chapter 28), in Pathology of the Human Placenta. 2002, Springer-Verlag: New York. p. 920-927.
Salafia, C.M., et al., Relationship between placental histologic features and umbilical cord blood gases in preterm gestations. Am J Obstet Gynecol, 1995. 173(4): p. 1058-64.
Salafia, C.M., et al., Intrauterine growth restriction in infants of less than thirty-two weeks' gestation: associated placental pathologic features. Am J Obstet Gynecol, 1995. 173(4): p. 1049-57.
Salafia, C.M., et al., Maternal, placental, and neonatal associations with early germinal matrix/intraventricular hemorrhage in infants born before 32 weeks' gestation. Am J Perinatol, 1995. 12(6): p. 429-36. 117. Salafia, C.M., et al., Clinical correlations of patterns of placental pathology in preterm pre-eclampsia. Placenta, 1998. 19(1): p. 67-72.
Salafia, C.M., et al., Placental pathologic features of preterm preeclampsia. Am J Obstet Gynecol, 1995. 173(4): p. 1097-105.
Salafia, C.M., et al., Clinical correlations of patterns of placental pathology in preterm pre-eclampsia. Placenta, 1998. 19(1): p. 67-72.
Salafia, C.M., et al., Placental pathology of absent and reversed end-diastolic flow in growth-restricted fetuses. Obstet Gynecol, 1997. 90(5): p. 830-6.
Viscardi, R.M. and C.C. Sun, Placental lesion multiplicity: risk factor for IUGR and neonatal cranial ultrasound abnormalities. Early Hum Dev, 2001. 62(1): p. 1-10.
Hagberg, H., D. Peebles, and C. Mallard, Models of white matter injury: comparison of infectious, hypoxic-ischemic, and excitotoxic insults. Ment Retard Dev Disabil Res Rev, 2002. 8(1): p. 30-8.
K. B., Examination of the Placenta, prepared for the Collaborative Study on Cerebral Palsy, Mental retardation and other Neurological and Sensory Disorders of Infancy and Childhood, N.I.o.N.D.a. Blindness, Editor. 1961, US Department of Health, Education and Welfare.
Kuh, D. and R. Hardy, A life course approach to women's health. Life course approach to adult health ; No. 1. 2002, Oxford ; New York: Oxford University Press. xvi, 419 p.
Niswander, K. and M. Gordon, The Collaborative Perinatal Study of the National Institute of Neurological Diseases and Stroke: The Women and Their Pregnancies. 1972, Philadelphia, PA: W.B. Saunders.
Myrianthopoulos, N.C. and K.S. French, An application of the U.S. Bureau of the Census socioeconomic index to a large, diversified patient population. Soc Sci Med, 1968. 2(3): p. 283-99.
Baik, I., et al., Association of fetal hormone levels with stem cell potential: evidence for early life roots of human cancer. Cancer Res, 2005. 65(1): p. 358-63.
Lagiou, P., et al., Birthweight differences between USA and China and their relevance to breast cancer aetiology. Int J Epidemiol, 2003. 32(2): p. 193-8.
Warren, Paul. "From Ubiquitous Computing to Ubiquitous Intelligence," Journal BT Technology, Springer Netherlands, Issue vol. 22, No. 2/Apr. 2004, pp. 28-38 [retireved on Jul. 2, 2007]. Retrieved from the Internet: URL:http://www.tcn-uk.org/siteassets/documents/TCN/1/B/1BB94F36-032A-47D4-BC1E-336FABCC40C8/1/2004%20vol3prt1%20Jan%20(5).pdf>.
Utzinger et al., "Fiber Optic Probes for Biomedical Optical Spectroscopy", Journal of Biomedical Optics, Jan. 2003, p. 3.
Johansson, et al., "System for Integrated Interstitial Photodynamic Therapy and Dosimetric Monitoring", Proceedings of the SPIE—The International Society for Optical Engineering, Jan. 2005, pp. 130-140, vol. 5689, No. 1.

* cited by examiner

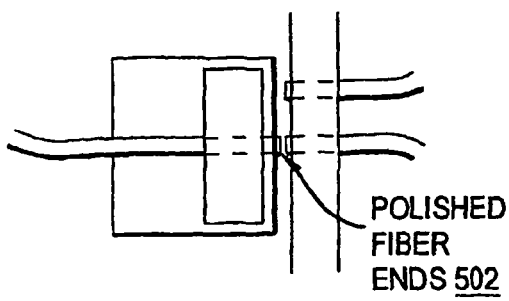
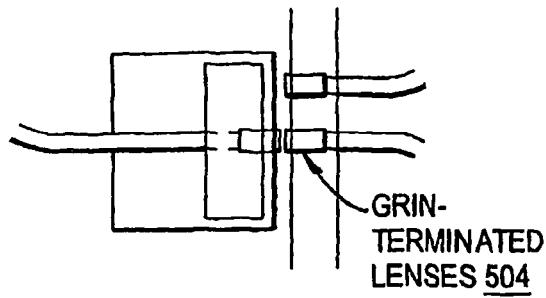
FIG. 5A
FIG. 5B
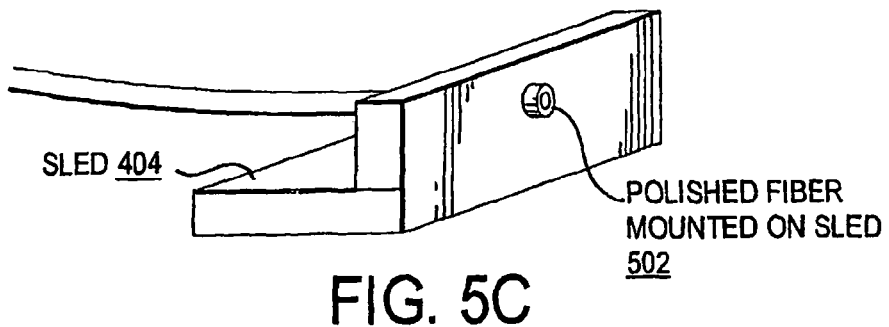
FIG. 5C
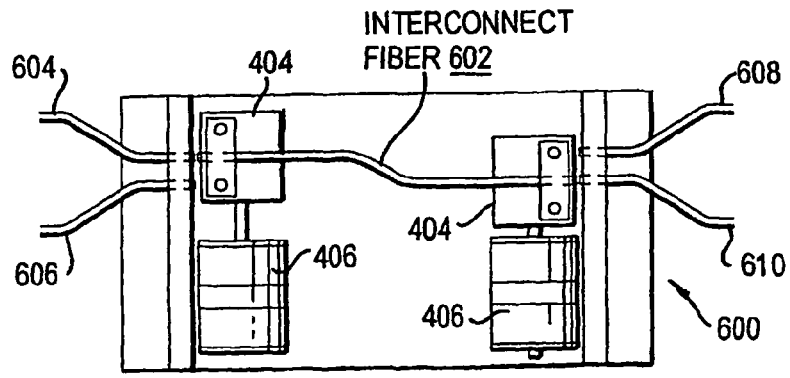
FIG. 6

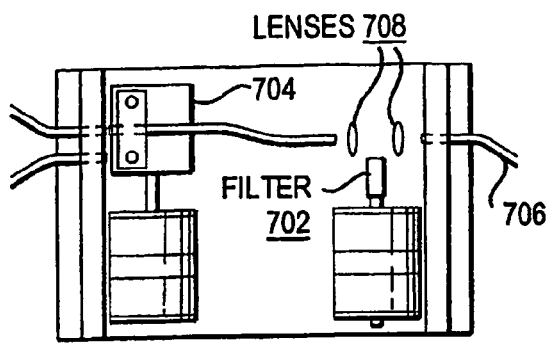
FIG. 7A
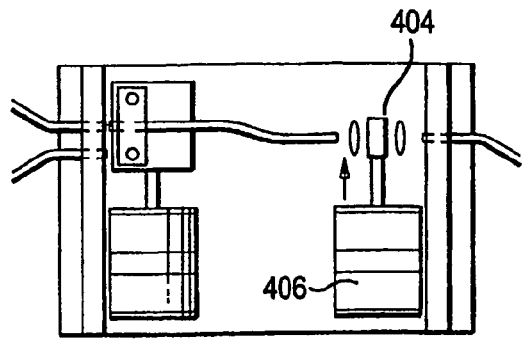
FIG. 7B
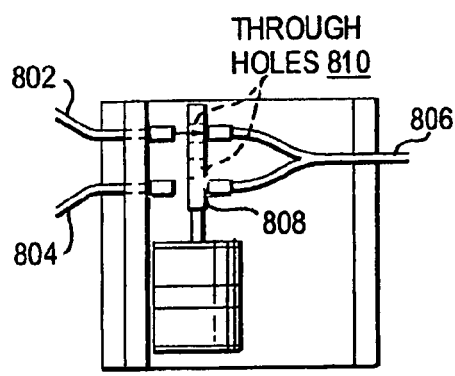
FIG. 8A
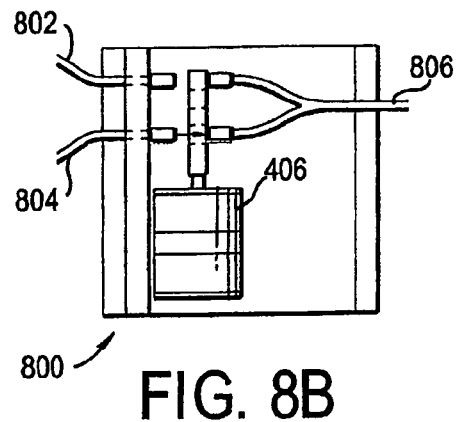
FIG. 8B
FIG. 9
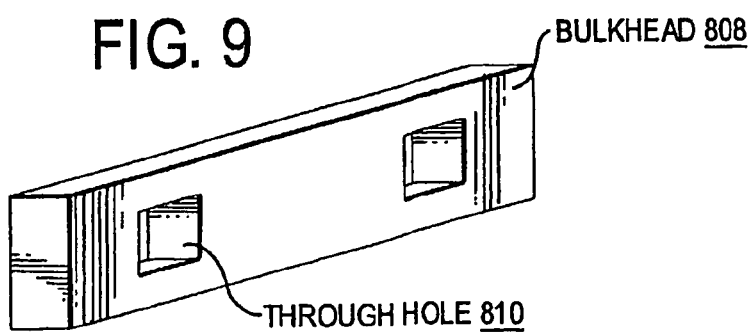

US 9,044,140 B2

PHOTODYNAMIC THERAPY WITH SPATIALLY RESOLVED DUAL SPECTROSCOPIC MONITORING

REFERENCE TO RELATED APPLICATION

The present application claims the benefit of U.S. Provisional Patent Application No. 60/583,786, filed Jun. 30, 2004, whose disclosure is hereby incorporated by reference in its entirety into the present disclosure.

STATEMENT OF GOVERNMENT INTEREST

The research leading to the present invention was supported by the Roswell Park Cancer Institute/NIH under Grant No. P01 CA55719. The government has certain rights in the invention.

FIELD OF THE INVENTION

The present invention is directed to photodynamic therapy (PDT) and more particularly to a method and apparatus for accurate, real-time determination of a therapeutic dose delivered by photodynamic therapy.

DESCRIPTION OF RELATED ART

The accurate, real-time determination of therapeutic dose delivered by photodynamic therapy (PDT) is an area of active research and clinical importance. Photosensitizer evolution, including photobleaching and photoproduct formation, and accumulation of endogenous porphyrins provide attractive implicit dose metrics, as these processes are mediated by similar photochemistry as dose deposition and report cellular damage, respectively. Reflectance spectroscopy can similarly report blood volume and hemoglobin oxygen saturation.

However, the accuracy of known techniques is still not sufficient. In particular, living human tissue has dynamic optical properties which may reduce the accuracy.

SUMMARY OF THE INVENTION

It is an object of the invention to provide real-time in vivo determination of photodynamic therapy dose metrics and tissue optical properties.

It is another object to correct for the dynamic optical properties of tissue.

To achieve the above and other objects, the present invention is directed to an apparatus for real-time determination of photodynamic therapy dosimetry in vivo, employing measurements of fluorescence emission spectra corrected for the effects of dynamic tissue optical properties using white light diffuse reflectance. This system accurately measures photosensitizer photobleaching, photoproduct formation, and tissue oxygenation, all of which are useful as dose metrics.

Compact instrumentation is developed that controls delivery and monitoring of PDT dose. In at least one embodiment, the instrumentation provides 405 nm fluorescence excitation light to two spatially-resolved points on the skin, delivered through fiber-pigtailed LEDs terminated with GRIN microlenses. One point is located inside the PDT target lesion and the other in the perilesion margin. The fluorescence spectra generated from sensitizer, photoproducts, autofluorescence, and various endogenous porphyrins are measured from both points, concurrently with excitation. Emission spectra from these points are corrected for the effects of tissue optical properties with division by white light reflectance spectra delivered through the treatment fiber. Spectral fitting reports fluorophore concentrations and blood oxygenation. This instrumentation employs multimode fiber switches and time multiplexing to deliver the treatment beam at 635 nm, fluorescence excitation beam at 405 nm, and white light interrogation beam while monitoring the aforementioned dose metrics with a pair of thermoelectrically cooled spectrometers.

The present invention can provide real-time determination of photodynamic therapy dosimetry in vivo during PDT treatment. The fluorescence spectra and white light reflectance are measured from each point during brief interruption of the treatment beam. Emission spectra are corrected for the effects of tissue optical properties with division by white light reflectance spectra, and spectral fitting is used to accurately characterize photosensitizer photobleaching, photoproduct formation, blood volume, and tissue oxygenation, all of which are useful as dose metrics.

BRIEF DESCRIPTION OF THE DRAWINGS

Preferred embodiments of the invention will be set forth in detail with reference to the drawings, in which:

FIGS. 5A-5C show variations of the fiber terminations in the switch of FIGS. 4A and 4B;

FIG. 6 shows a 2×2 fiber optic switch based on the fiber optic switch of FIGS. 4A and 4B;

FIGS. 7A and 7B show a variation of the switch of FIGS. 4A and 4B with a filter which can be moved into or out of the light beam;

FIGS. 8A and 8B show a further modification of the switch of FIGS. 4A and 4B;

FIG. 9 is a perspective view showing a bulkhead used in the switch of FIGS. 8A and 8B;

DETAILED DESCRIPTION OF THE PREFERRED EMBODIMENTS

Figure 1:
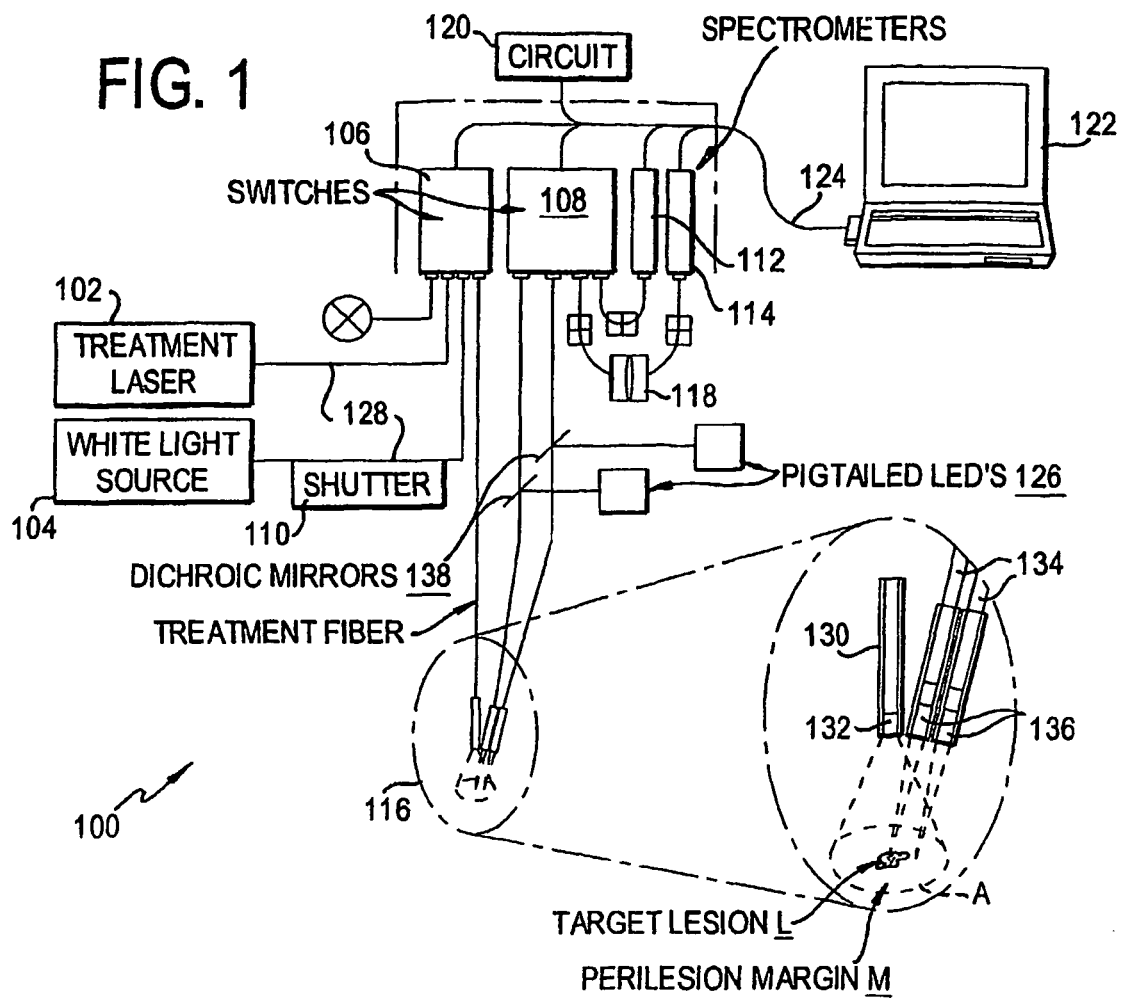
FIG. 1 is a schematic diagram showing an instrument according to a first preferred embodiment of the invention.

Preferred embodiments of the present invention will be set forth in detail with reference to the drawings, in which like reference numerals refer to like elements or operational steps throughout.

An instrument according to a first preferred embodiment of the present invention is shown in FIG. 1 as 100. As shown, the instrument includes a treatment laser (such as a dye laser) 102, a white light source (such as a tungsten halogen or xenon lamp) 104, fiber optic switches 106, 108, a shutter 110, two thermoelectrically cooled spectrometers 112, 114, an optical probe 116, an optical filter 118, circuitry 120, housings (not shown), and a computer 122. The computer 122 and the spectrometers 112, 114 communicate through a USB cable connection 124. Each of the spectrometers 112, 114 has reserved auxiliary (AUX) pins on its on-board circuitry. The AUX pins are connected to the LEDs 126, shutter 110, and fiber optic switches 106, 108 via external circuitry 120. Transistor-transistor logic (TTL) pulses transmit from the AUX pins to the circuitry 120.

In a delivery arm of the instrument 100, the white light source 104 and treatment laser 102 are coupled via fibers 128 into the 2×1 fiber optic switch 106. The output of this switch 106 is coupled via a fiber 130 to part of the optical probe 116 and is terminated with a microlens 132.

In the detection arm, two more optical fibers 134 terminated with microlenses 136 are in the probe. Each of the two fibers 134 is directed to a housing (not shown) with a dichroic optical filter 138. The reflection path of the filter housing contains an LED 126, and the transmission path contains a secondary optical fiber 140. The secondary optical fibers 140 are connected to the 2×2 optical switch 108. One of the two outputs of the 2×2 switch 108 is directed to the first spectrometer 112, and the second output is directed to the optical filter 118 and then to the second spectrometer 114.

The treatment area A includes two regions, a target lesion region L and a perilesion margin region M.

The computer 122 determines which of two states the first fiber optic switch 106 is in and the state of the white light shutter 110. Depending on the states of the switch 106 and shutter 110, the light is blocked, white light is transmitted through the treatment fiber 130, or laser light from the treatment laser 102 is transmitted though the treatment fiber 130. Light transmitted through the treatment fiber 130 is directed onto the treatment area A, comprising both the lesion region L and the perilesion region M. The treatment areas may have different optical, chemical or physiological properties.

Light emitted or reflected from the area A is collected by the two optical fibers 134 terminated with microlenses 136. One of the optical fibers 134 collects primarily from the target lesion region L, and the other fiber 134 collects primarily from the perilesion margin region M. Light may also be generated by the LEDs 126 in the detection arm. Light generated by the LEDs 126 will be reflected off the dichroic mirror 138 and transmitted through the optical fibers 134 and directed through the microlenses 136 onto the corresponding treatment regions L, M. Light omitted or reflected from these regions will be collected by the fibers 134 and directed onto the dichroic mirror 138. Light that is at a different wavelength from the LED sources 126 will be transmitted through the filter 138. Light transmitted through the secondary fibers 140 is directed into the 2×2 optical switch 108. Depending on the state of the 2×2 optical switch 108, light from either of the two secondary detection fibers 140 can be directed either through another optical filter 118 followed by a spectrometer 114 or directly into a spectrometer 112.

Up to three measurements can be made for each of two spatially resolved locations during photodynamic therapy. The laser source is used as a treatment beam. Light from this source is directed into the treatment area and activates photoactive drugs within that area.

Treatment beam excited fluorescence can be measured. Some of the absorbed laser light may be emitted as fluorescence. By directing collected light through the filtered path of the system before the spectrometer, the fluorescent signal can be evaluated without the spectrometer being optically saturated by the treatment laser. Therefore, with the first switch transmitting the laser and the second switch directing light collected from the treatment area region of interest, spatially resolved fluorescence from that region can be measured.

In measuring 405 nm excited fluorescent signals, the fluorescent signals of interest are highly excited by light emitted by the LED sources. By using the first fiber switch and shutter to stop the laser and white sources and using pulses to turn on the LED source, the 405 nm light can be directed onto either treatment region of interest, and excited fluorescence can be collected through that same path and directed by the 2×2 fiber switch directly to the non-filtered spectrometer path. Therefore, a spatially resolved measurement of fluorescence can be made.

The reflected spectrum of a white light source provides information about tissue optical properties, blood volume, and blood oxygenation. White light can be directed through the first optical switch on the treatment area, and the reflected signal can be collected by the detection arm. Either of the two fibers in the detection path can be directed into the non-filtered spectrometer, and the spatially resolved white light reflectance can be measured. The computer 122 receives detection signals for all types of reflected light and uses the reflected white light to correct the detection signals for the dynamic optical properties of the tissue, particularly the spectral reflectivity.

During the measurements listed, data are transmitted from the spectrometers into the computer, where characteristics about the treatment regions are stored and analyzed. Analysis of the data from these measurements can be fed back into the system to control the timing of the measurements and the treatment.

Figure 2:
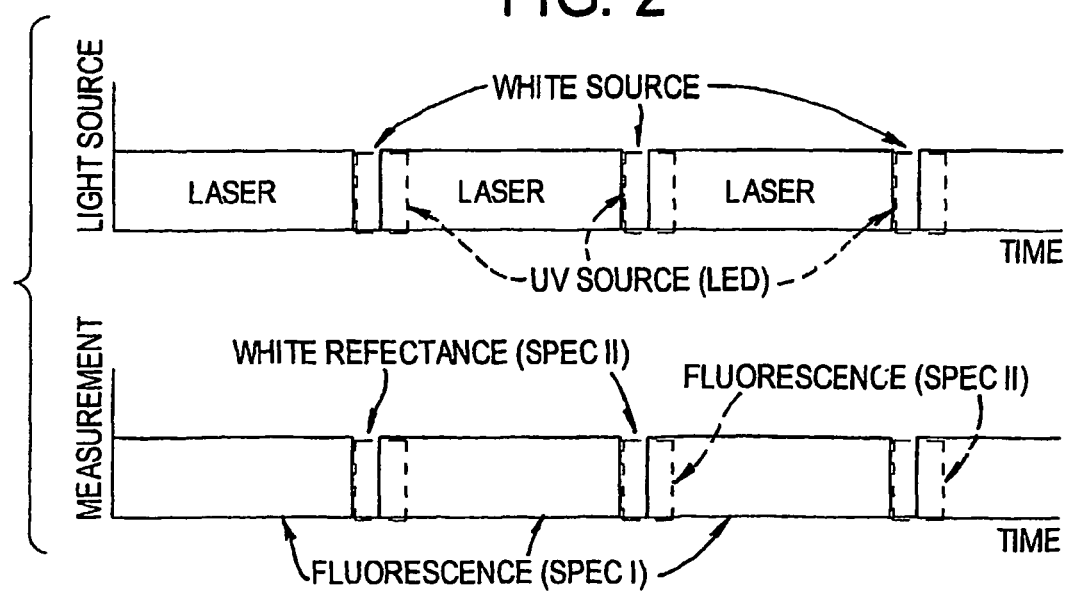
FIG. 2 is a timing chart showing a timing of operation of the instrument of FIG. 1.

An example of timing is shown in FIG. 2. The timing of the light source alternates among the laser, the white light source, and the LED (an ultraviolet source). The corresponding time periods for measurement are fluorescence from the laser, reflectance from the white light, and fluorescence from the LED. With those measurements, it is possible to correct for dynamic tissue optical characteristics.

Figure 3:
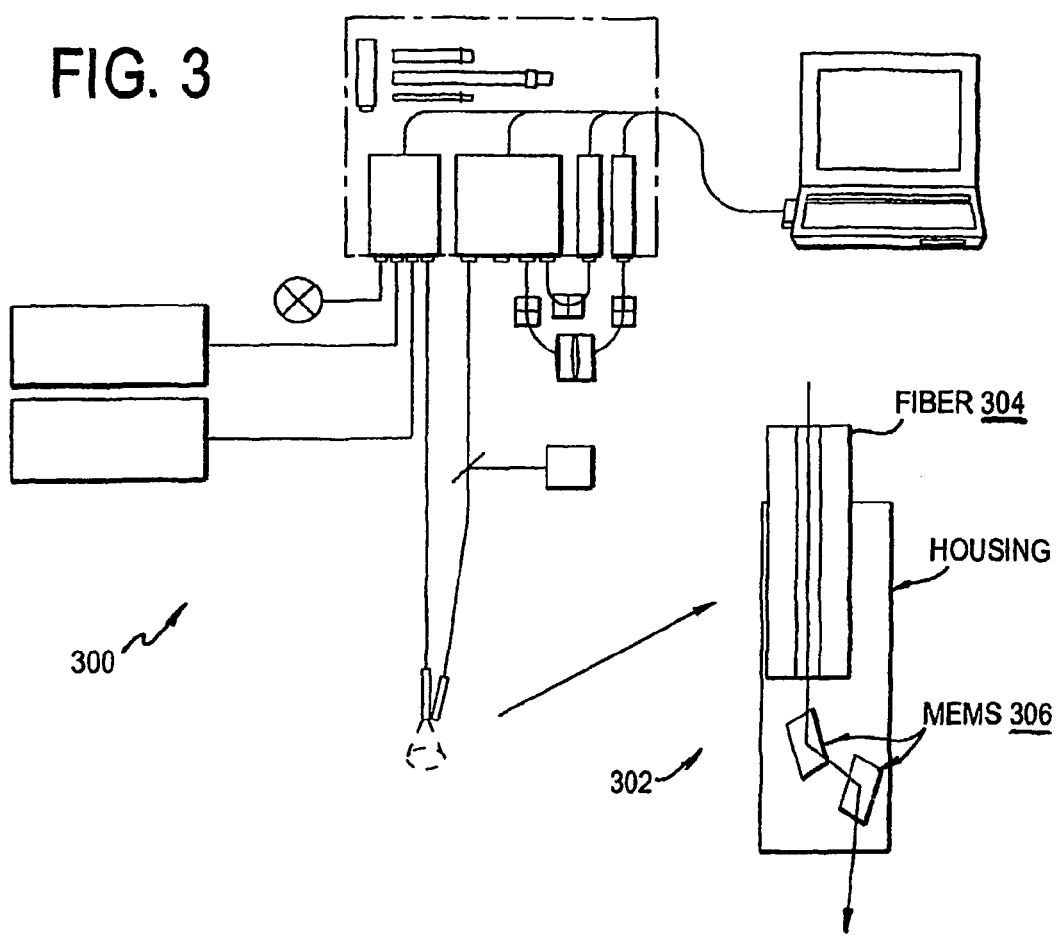
FIG. 3 is a schematic diagram showing an instrument according to a second preferred embodiment of the invention.

A second preferred embodiment, using an optical probe, will now be described. An instrument according to the second preferred embodiment is shown in FIG. 3 as 300. Except as noted below, the instrument 300 can be constructed and used like the instrument 100.

The optical probe 302 is capable of two-point spatial resolution. A single or plurality of optical fibers 304 can be used in concert with either a single or plurality of MEMS (micro-electro-mechanical systems) scanning mirrors 306 in a housing 308 to scan the treatment area. At each location (pixel) in the scan analogous measurements to those above can be performed. Also, the delivery of the laser, white light, and LED sources may be delivered through the same optical probe that is doing the collection depending on switching configuration.

Either of the preferred embodiments can use a variety of switches, such as the following.

Several embodiments of large diameter multimode fiber switches (the switches 106 and 108 of FIGS. 1 and 3) are provided, as illustrated in FIGS. 4A through 9. The purpose of the switches is to control the flow of light through the system, as previously disclosed. In addition, some embodiments contain in-line filters which can be moved into or out of the path in order to control the light transmitted through the system.

Figure 4A:
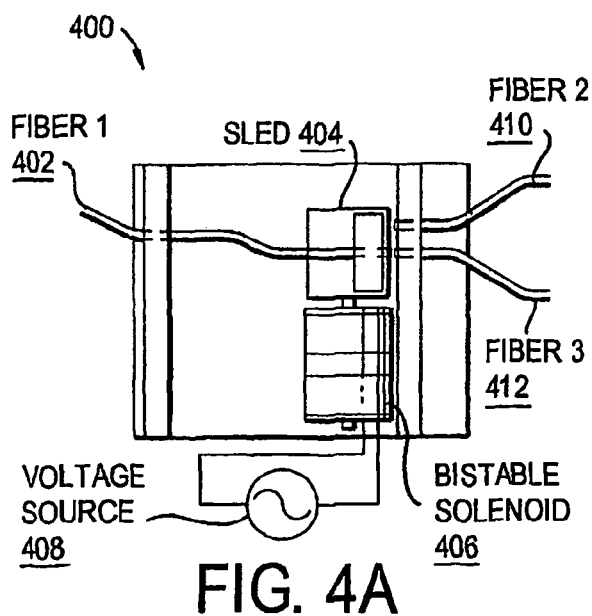
FIGS. 4A and 4B show a 1×2 fiber optic switch usable in the embodiment of FIG. 1 or that of FIG. 3.
Figure 4B:
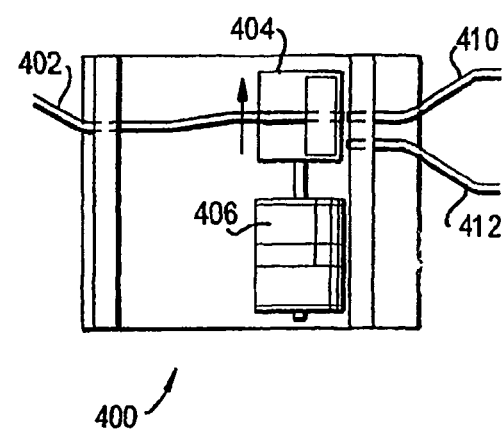

FIG. 4A shows a top view of a 1×2 fiber optic switch 400 in which an optical fiber 402 is mounted on a translating sled 404 that can be translated by a linear actuator (bistable solenoid) 406 by applying a voltage from a voltage source 408 across electrical leads. In this embodiment using a bistable solenoid 406, a voltage pulse across one set of leads translates the sled 404 into a first position. Permanent magnets within the solenoid 406 latch the device in place so that it is stable and requires no additional electrical source to hold it in place. In this position, the fiber 402 is in close proximity to the fiber 412 and provides optical throughput from the fiber 402 to the fiber 412 (or vice versa). Application of a voltage pulse across a second set of leads (not shown) translates the sled 404 to a second position, as shown in FIG. 4B, where a second set of permanent magnets holds the sled 404 in place and throughput between the fiber 402 and a fiber 410 is obtained. A precision linear slide (not shown) holds the sled 404 very precisely in two dimensions to reduce fiber alignment errors otherwise imparted by the slop in the axle of the bistable solenoid 406.

FIGS. 5A-5C show a magnified view of the sled 404 and the alignment of the optical fibers 402, 410, 412. In FIG. 5A, the fibers used have polished ends 502 and are coupled by placing them in close proximity. In FIG. 5B, the fibers are terminated with lenses (GRIN lenses) 504 which collimate the beam and allow efficient coupling at spacing prohibitive for polished fiber coupling. An alternative embodiment of that shown in FIG. 5B would include traditional lenses or ball lenses. FIG. 5C shows a perspective view of the sled holding an optical fiber.

FIG. 6 shows a 2×2 switch 600 using the same base components as used for the 1×2 switches of FIGS. 4A and 4B. In this embodiment, an interconnecting fiber 602 allows either of the two input fibers 604, 606 to be connected to either of the two output fibers 608, 610 by controlling the positions of the sleds 404 with two bistable solenoids 406. The basic 1×2 switch can be multiplexed together as in the 2×2 switch to increase number of channels that can be switched.

FIGS. 7A and 7B show a removable in-line filter 702 incorporated into a 1×2 switch 700 based on the previous design. In this embodiment, a fiber 704 from the 1×2 switch is coupled to a second fiber 704 with lenses 706. A filter 702 mounted onto a sled 404 (as previously described) can then be translated into or out of the beam path using a solenoid 406. In this way, light transmitted through the system can be modified in intensity, spectral content, or polarization depending on filter choice. FIG. 7A shows this device with the filter not in the path of the light, and FIG. 7B shows this device with the filter in the path of the light. Again, a precision linear guide may be used to improve system repeatability and robustness.

FIGS. 8A and 8B show an alternative 1×2 switch embodiment 800 in which two lens-terminated fibers 802, 804 are mounted in the switch 800 and aligned to the two input ends of a y-coupled fiber 806. Switching between throughput of fibers is accomplished by translating a bulkhead 808 with through holes 810. In FIG. 8A, the bulkhead 808 is in a first position, and light transmitted through a first fiber 802 travels through a through hole 810 in the bulkhead and is coupled into the output by the y-coupler 806. Light transmitted through the second fiber 804 is blocked by the bulkhead 808. FIG. 8B shows the device 800 after the bistable solenoid 406 is used to switch the position of the bulkhead 808. In this state, light transmitted through the first fiber 802 is blocked by the bulkhead 808, and light transmitted through the second fiber 804 is transmitted through a through hole 810 and is coupled into the output fiber by the y-coupler 806. A perspective view of the bulkhead 808 with through holes 810 is illustrated in FIG. 9. Similarly, this basic switch unit can be multiplexed to achieve a higher number of channels and can also have in-line filters incorporated for additional functionality.

Use of a precision linear slide to improve throughput repeatability and lifetime and inclusion of coupling optics to improve robustness separates this system from known prior art examples. No prior art incorporating y-couplers and bulkheads with through holes is known. Switches incorporating bistable solenoids can be purchased commercially from Fibersense & Signals Inc., San Jose, Calif., U.S.A.

Figure 10:
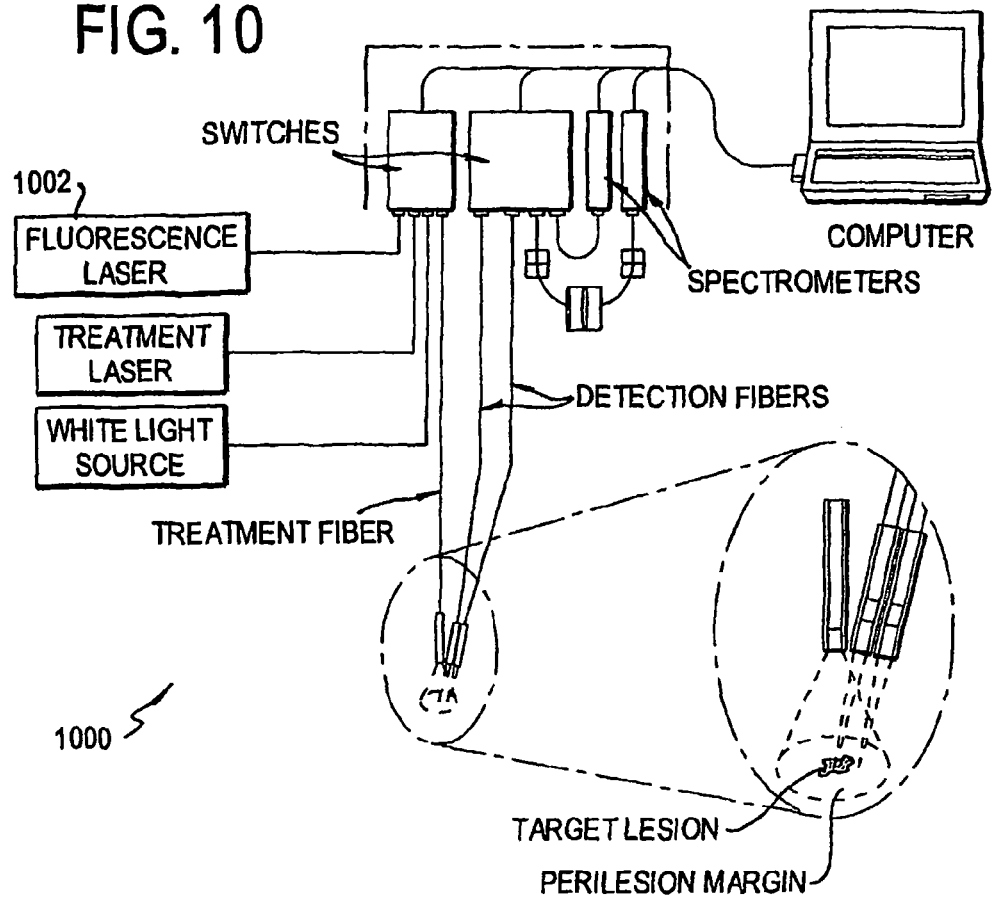
FIG. 10 shows an instrument according to a third preferred embodiment of the present invention.
Figure 11:
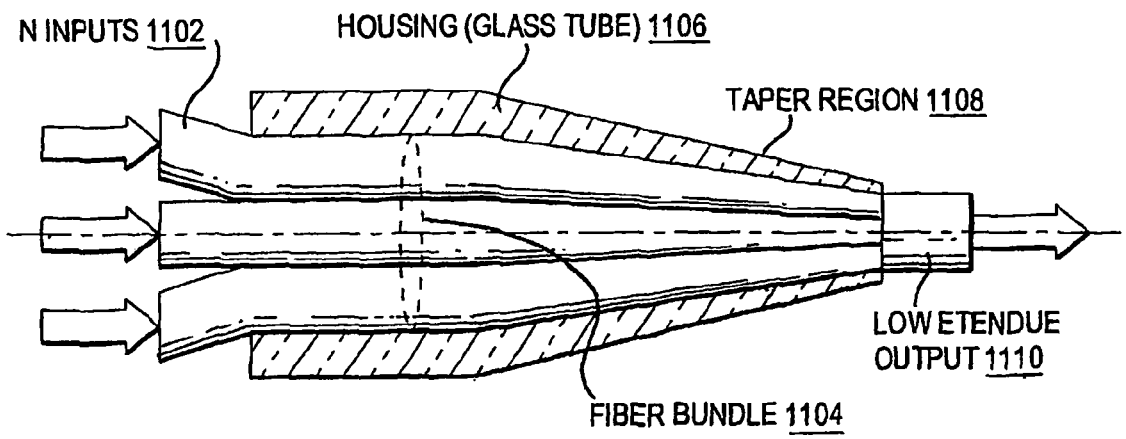
FIG. 11 shows an alternative fiber coupler usable with the embodiment of FIG. 10.

FIG. 10 shows a third preferred embodiment of the invention. In the third preferred embodiment, the instrument 1000 can be constructed and used like the instrument 100 of FIG. 1, except that additional light sources, such as a fluorescence laser 1002, are coupled into the system and transmitted through the treatment fiber. Such additional sources may be coupled with multiplexed switches, as described above. In a variation of the third preferred embodiment, sources may be coupled into the system by butt-coupling multiple fiber sources into the treatment source. A known type of coupling is shown in FIG. 11 as 1100, in which input fibers 1102 are formed into a fiber bundle 1104 in a housing 1106 and tapered to form a taper region 1108 leading to the output fiber 1110. In this case, the source fibers used would have smaller diameters than the treatment fiber, and the sources would be switched on and off, or shuttered on and off upstream of the coupling. In this way, multiple sources can be used to interrogate the target tissue without much added complexity. It is an advantage of this embodiment that the sources are transmitted to the tissue surface in the same geometry which simplifies computational analysis and interpretation of resulting measurements.

While preferred embodiments and variations thereon have been set forth above, those skilled in the art who have reviewed the present disclosure will readily appreciate that other embodiments can be realized within the scope of the invention. For example, wavelengths and other numerical values are illustrative rather than limiting. Therefore, the present invention should be construed as limited only by the appended claims.

We claim:

1. An instrument for performing photodynamic therapy on a treatment area comprising a target lesion and a perilesion margin of a living patient, the instrument comprising:
    light sources for providing treatment light for activating photoactive drugs within the treatment area, broadband light for creating a first reflected light spectrum from the target lesion and a second reflected light spectrum from the perilesion margin, and fluorescence excitation light for creating a first fluorescence from the target lesion and a second fluorescence from the perilesion margin;
    first optics for causing the treatment light, the broadband light and the fluorescence excitation light to be incident on the treatment area, whereby the broadband light is reflected from the treatment area and the fluorescence excitation light causes the treatment area to emit fluorescence;
    second optics for receiving the first reflected light spectrum from the target lesion and the second reflected light spectrum from the perilesion margin and the first fluorescence from the target lesion and the second fluorescence from the perilesion margin;
    a first spectrometer for receiving the first reflected light spectrum and the second reflected light spectrum from the second optics and for producing a signal representing the first reflected light spectrum and the second reflected light spectrum;
    a second spectrometer for receiving the first fluorescence and the second fluorescence from the second optics and for producing a signal representing the first fluorescence and the second fluorescence; and
    a computer, receiving the signals from the first and second spectrometers, for correcting the spectrum of the first fluorescence and the second fluorescence in accordance with the first reflected light spectrum and the second reflected light spectrum respectively and for providing the corrected first fluorescence and second fluorescence light spectrum for treatment optimization.

2. The instrument of claim 1, wherein the first optics comprise an optical switch for time-multiplexing the treatment light and the broadband light.

3. The instrument of claim 2, wherein the optical switch comprises:
   a first optical fiber for supplying the treatment light to the optical switch;
   a second optical fiber for supplying the broadband light to the optical switch;
   a third optical fiber for selectively receiving the treatment light or the broadband light;
   a sled for moving the third optical fiber to be in optical communication with the first optical fiber or the second optical fiber; and
   a bistable solenoid for moving the sled.

4. The instrument of claim 3, wherein each of the first, second and third optical fibers comprises a polished fiber end.

5. The instrument of claim 3, wherein each of the first, second and third optical fibers is terminated by a lens.

6. The instrument of claim 5, wherein the lens is a gradient index lens.

7. The instrument of claim 2, wherein the optical switch comprises:
   a first optical fiber for supplying the treatment light to the optical switch;
   a second optical fiber for supplying the broadband light to the optical switch;
   a Y coupler for selectively receiving the treatment light or the broadband light;
   a bulkhead, having at least one through hole, for selectively blocking light from the first optical fiber or the second optical fiber to the Y coupler;
   a sled for moving the bulkhead to block the light from the first optical fiber or the second optical fiber; and
   a bistable solenoid for moving the sled.

8. The instrument of claim 2, wherein the optical switch time-multiplexes the treatment light, the broadband light and the fluorescence excitation light.

9. The instrument of claim 1, wherein the first optics comprise spatially resolving optics for causing the fluorescence excitation light to be incident on a plurality of locations in the region of interest.

10. The instrument of claim 9, wherein the spatially resolving optics comprise a plurality of optical fibers, each for directing a portion of the fluorescence excitation light onto one of the plurality of locations.

11. The instrument of claim 10, wherein each of the plurality of optical fibers in the spatially receiving optics is terminated by a lens.

12. The instrument of claim 11, wherein the lens is a gradient index lens.

13. The instrument of claim 10, wherein each of the plurality of optical fibers receives the reflected broadband light and the fluorescence emission light from said one of the plurality of locations and supplies the reflected broadband light and the fluorescence emission light to the second optics.

14. The instrument of claim 13, wherein the second optics comprise an optical switch for selectively applying the reflected broadband light and the fluorescence emission light from each of the plurality of optical fibers selectively to each of the first and second spectrometers.

15. The instrument of claim 9, wherein the spatially resolving optics comprise a scanning system for scanning the fluorescence excitation light onto the plurality of locations.

16. The instrument of claim 15, wherein the scanning system comprises at least one movable mirror.

17. The instrument of claim 1, wherein the second optics comprise a dichroic mirror for spectrally separating the fluorescence excitation light from the fluorescence emission light.

18. The instrument of claim 17, wherein the first optics apply the fluorescence excitation light to the region of interest by using the dichroic mirror.

* * * * *